United States Patent [19]
Ries

[11] Patent Number: 5,217,738
[45] Date of Patent: Jun. 8, 1993

[54] METHOD FOR THE TREATMENT OF HARVESTED PLANT PARTS WITH L(+) ADENOSINE OR 1-TRIACONTANOL

[75] Inventor: Stanley K. Ries, East Lansing, Mich.

[73] Assignee: Board of Trustees operating Michigan State University, East Lansing, Mich.

[21] Appl. No.: 869,958

[22] Filed: Apr. 17, 1992

[51] Int. Cl.$^5$ .................. A01N 43/08; A01N 31/02; A23B 7/154

[52] U.S. Cl. ................................. 426/302; 426/102; 426/442; 426/615; 504/136; 504/241; 504/353

[58] Field of Search .............. 71/88, 122; 426/102, 426/273, 302

[56] References Cited

U.S. PATENT DOCUMENTS

| | | | |
|---|---|---|---|
| 4,150,970 | 4/1979 | Ries et al. | 71/122 |
| 4,333,758 | 6/1982 | Welebir | 71/80 |
| 4,741,754 | 5/1988 | Ries | 71/122 |
| 4,849,012 | 7/1989 | Wilson | 71/122 |
| 5,009,698 | 4/1991 | Ries et al. | 71/92 |

OTHER PUBLICATIONS

Ries et al. "9-β-L(+) Adenosine: A New Naturally Occurring Plant Growth Substance Elicite by Triacontanol in Rice", Plant Growth Regulation 9: 263–273, 1990.
Wilson, W. C. et al., Methods for reducing acidity in citrus fruit, Proc. Fla. State Hortic. Soc. 101: 157–161 (1988).
Houtz, R. L., Dev. and characterization of an in vitro system responsive to 1-triacontanol, M. S. Thesis, MSU, East Lansing, Mich. (1980).
Ries, S. K., et al., Plant Growth Reg. 9, 263–273 (1990).
Monselise, S. P., Scientia Hortic 11: 151–162 (1979).
Deszyck, E. J., et al., J. Amer. Soc. Hort. Sci. 75: 266–270 (1959).
Bittenbender H. C., et al., Plant Physiol. 61: 851–854 (1978).
Ries et al., J. Plant Growth Regul. 1: 117–127 (1982).

*Primary Examiner*—Glennon H. Hollrah
*Assistant Examiner*—S. Mark Clardy
*Attorney, Agent, or Firm*—Ian C. McLeod

[57] ABSTRACT

A method for the treatment of a harvested plant part with L(+) adenosine or 1-triacontanol to improve the quality of the parts, such as fruit, vegetables (including root vegetables) and leaves. The method includes applying the L(+) adenosine or 1-triacontanol to the part of the plant after harvest of the fruit or vegetable. The acidity or sugar content of the plant part and thus the sugar to acid ratio is particularly affected by the treatment.

9 Claims, 3 Drawing Sheets

METHOD FOR THE TREATMENT OF HARVESTED PLANT PARTS WITH L(+) ADENOSINE OR 1-TRIACONTANOL

BACKGROUND OF THE INVENTION (1) Field of the Invention

The present invention relates to the treatment of parts of a plant after they have been removed from the plant to improve the quality of the parts, particularly to reduce or increase the acidity and sugar content in the part. In particular, the present invention relates to the use of L(+) adenosine and 1-triacontanol to treat the plant part to improve the quality of the part.

(2) Prior Art

U.S. Pat. No. 4,849,012 to Wilson describes the use of 1-triacontanol (TRIA) applied to the trees with the fruits to increase the sugar content in oranges. Tests with oranges (Citrus sinensis L.) showed that this increase in sugar was translated into higher brix/acid ratios in the fruit when entire trees were sprayed in the grove as described in U.S. Pat. No. 4,849,012 and Wilson, W. C., et al., Methods for reducing acidity in citrus fruit, Proc. Fla. State Hortic. Soc. 101:157-161 (1988). These increases are economically important to the citrus industry because the value and maturity of citrus fruit is partially determined by its brix/acid ratio. Brix, or % soluble solids, is used as a measurement of the sugar content since sugar is the main component.

The use of TRIA and TRIM to stimulate plant growth is described in U.S. Pat. Nos. 4,150,970 to Ries et al and 4,741,754 to Ries. U.S. Pat. No. 4,333,758 to Welebir also shows TRIA compositions used for this purpose. Foliar applications of micromolar concentrations of TRIA stimulated an increase in reducing sugars and total reducible nitrogen in both whole plants and cell free systems (Houtz, R. L., Development and characterization of an in vitro system responsive to 1-triacontanol. M. S. Thesis, Michigan State University, East Lansing, Mich. (1980)).

U.S. Pat. No. 5,009,698 to Ries, Wert and Nair, describes the use of L(+)adenosine, isolated from TRIM initially and then derived from chemical sources, to stimulate the growth of a plant. The L(+)adenosine is applied early in the growth of the plant and produces significant yield improvements.

Triacontanol (TRIA) is used on millions of hectares to increase crop yield, particularly in Asia. In controlled environment studies, synthetic L(+) adenosine was found to increase the rate of growth of rice seedlings as measured by total dry weight gain, more than 50% within 24 hours of a foliar application of 0.01 to 100.0 $\mu g \cdot L^{-1}$ ($3.7 \times 10^{-11}$ to $10^{-7}$ M) (Ries, S. K., et al., Plant Growth Reg. 9, 263 (1990)). L(+) adenosine is more consistent than TRIA.

The improvement of fruit quality through the use of chemicals has also received attention, particularly as it pertains to citrus fruits (Monselise, S. P., Scientia Hortic. 11:151-162 (1979)). Arsenic containing compounds, particularly lead arsenate, are widely used in grapefruit (Citrus paradisi Macfadyen) to lower acid and increase the brix/acid ratio (Deszyck, E. J., et al., J. Amer. Soc. Hort. Sci. 75:266-270 (1959)). Many other chemicals are now being tested for this purpose (Tenzer, A. I., Proc Plant Growth Reg. Soc. Amer. 14:316-325 (1987); and 22, 23 and U.S. Pat. No. 4,849,012.

Arsanilic acid has been tested as a substitute for lead arsenate because of concerns about the safety of using inorganic arsenical compounds on food crops. In tests on grapefruit, arsanilic acid was found to increase the brix/acid ratio by decreasing the total acidity, in doses ranging 500 to 6000 mg/liter with 1000-1500 mg/liter being the most effective.

While arsenical compounds have improved the quality of grapefruit, they are not legal for use on oranges because they cause an extreme reduction in acidity [23]. For this reason, other plant growth regulators are now being investigated. In recent trials using foliar sprays before harvest on 'Hamlin' and 'Valencia' oranges, TRIA reduced the total acidity by an average of 17.5%, increased the brix an average of 16.3%, and increased the brix/acid ratio an average of 41.5% using concentrations of 0.67 and 1.33 ppb. (Wilson, W. C., et al., Methods for reducing acidity in citrus fruit, Proc. Fla. State Hortic. Soc. 101:157-161 (1988)). Other Commercial plant growth regulators such as Citrus 10 and NF-10 are also being tested (Tenzer A. I., Proc. Plant Growth Reg. Soc. 14:316-325 (1987); and (Wilson, W. C., et al., Methods for reducing acidity in citrus fruit, Proc. Fla. State Hortic. Soc. 101:157-161 (1988)). The active compounds in these formulations are not known.

OBJECTS

It is therefore an object of the present invention to provide a method for improving the quality of a plant part after removal from the plant wherein the chemicals applied are non-toxic. Furthermore, it is an object of the present invention to provide a method which is safe, simple and economic for use in the field (farm, ranch or grove) or in the greenhouse. These and other objects will become increasingly apparent by reference to the following description and the drawings.

GENERAL DESCRIPTION

The present invention relates to a method for improving the quality of a part to be consumed which is removed from a plant which comprises: applying a growth stimulant selected from the group consisting of L(+) adenosine and 1-triacontanol to the plant after the part is removed in an amount sufficient to improve the quality of the part; holding the part until the quality of the part is improved prior to consumption of the part. Further the present invention relates to a method for changing a sugar to acid ratio in a part with such ratio which is removed from a plant to be consumed which comprises: applying a growth stimulant selected from L(+) adenosine and triacontanol and mixtures thereof to the part in an amount sufficient to modify the sugar to acid ratio of the part; holding the part until the sugar to acid ratio is changed prior to consumption. The L(+) adenosine is preferably used in amounts between about 0.01 and 10,000 µg per liter. The triacontanol is used in amounts between about 0.01 and 100 µg per liter.

This invention provides a method for treating fruits and vegetables after harvest with TRIA and its second messenger TRIM to modify the brix, total acidity, and brix/acid ratio. TRIM had been identified as 9-β-L(+) adenosine. Where the brix and acid can be changed after harvest, it is easier and more economical than applying a treatment prior to harvest. U.S. application Ser. No. 07/819,997, filed Jan. 13, 1992 shows the affects of applying L(+) adenosine prior to harvest of the plant part.

As with other plant growth regulator induced responses, many factors would influence the response. The variables controlled were chemical concentration, temperature after treatment, stage of crop maturity at treatment, and the time between treatment and termination of the experiment. All of these variables are well known to those skilled in the art and the most advantageous conditions can easily be determined for each plant species.

Both triacontanol and 9-β-L(+) adenosine applied after harvest change the brix (soluble solids) concentration and the total acidity of several horticultural crops; however, the results varied widely depending on the crop and the condition or quality of the samples. Factors which affected this response were species, stage of crop maturity at the time of treatment, chemical concentration applied, and length of time between treatment and termination of the experiment.

The stage of maturity of the crop when the chemical was applied influenced the magnitude of the response. In some experiments, TRIA was more active at an earlier stage and 9-β-L(+) adenosine was more active at a later stage of maturity. This indicates that the two chemicals may have different modes of entry into the fruit, particularly since they vary widely in their water solubility.

The response to concentration seems to be more complex than a standard dose response curve. Either there is no optimum concentration for achieving a response with most crops, or the tests were complicated by other factors, such as the chemicals passing through the cuticles in varying amounts.

The time dependent effects of the chemicals, which occurred when the fruits were treated and then stored, was the most complex response. In strawberries which lose soluble solids in storage over time, 9-β-L(+) adenosine slowed down the loss. In sweet cherries, where soluble solids increased during storage, the 9-β-L(+) adenosine increased the brix more compared to controls at the earliest sampling time.

It is not clear why TRIA and 9-β-L(+) adenosine change the soluble solids and total acidity in these crops, particularly since both chemicals increased and decreased the brix in the same species. Other research (Bittenbender, H. C., et al., Plant Physiol. 61:851–854 (1978); Houtz, R. L., Development and characterization of an in vitro system responsive to 1-triacontanol. M. S. Thesis, Michigan State Univ., East Lansing, Mich. (1980); and Ries, S. K. and V. Wert, J. Plant Growth Regul. 1:117–127 (1982)), indicates that TRIA usually increases reducing sugars in vitro, and reducing sugars and soluble carbohydrates in whole plants. This may be due to TRIA stimulating the hydrolysis of some storage product into sugar, which could also explain the increases in brix observed in many of these tests. The decreases in brix and total acidity observed in other experiments may be due to TRIA increasing the respiration in the sample and consuming soluble solids. The reason why one process would be favored over the other in the same species is unclear.

SPECIFIC DESCRIPTION

In the following Examples 1 to 8, fruits and vegetables were treated after harvest with dips or sprays of nanomolar concentrations of 1-triacontanol (TRIA) and 9-β-L(+) adenosine to determine the effect of these growth substances on the brix, total acidity, and the brix to acid ratio. 9-β-L(+) adenosine is the second messenger elicited by TRIA.

Both chemicals decreased the acidity and the sugar/acid ratio of tomatoes. Both chemicals increased the brix of strawberries in one test, but high concentrations of 9-β-L(+) adenosine decreased the brix in a second test. In one of two tests with carrots, TRIA increased the brix. Sweet cherries responded to both chemicals. TRIA increased the brix of 'Idared' apples and decreased the acidity of 'Mutsu' apples.

The stage of maturity at treatment, chemical concentration applied and length of storage influenced the response of the crop to TRIA and 9-β-L(+) adenosine. Several species showed no post-harvest response to treatment.

MATERIALS AND METHODS

Obtaining and Preparing Samples

The experiments were conducted by obtaining samples of several species of marketable fruits and vegetables, and then treating them by immersion or spraying to drip with TRIA or 9-β-L(+) adenosine. They were stored at a constant temperature for a predetermined length of time. After termination of the tests, the brix, (soluble solids), total acidity, and the brix/acid ratio were determined.

All crops tested were marketable fruit and vegetables of standard commercial cultivars. General information about the crops and experimental conditions used are summarized (Table 1).

TABLE 1

| | Cultivars and general experimental conditions for all crops tested. | | | |
|---|---|---|---|---|
| Crop | Cultivar or Type | Source[z] | Storage (°C.) | Sorting Criteria |
| Apples | Idared | HRC | 20 & 30 | Color/Size |
| | Mutsu | HRC | 30 | Color/Size |
| Asparagus | Viking | HRC | 20 | Size |
| Blueberries | Highbush | HRC | 20 | Color |
| Carrots | Regular | Greenhouse | 30 | Size/Shape |
| | Mini | Grocer | 30 | Size/Shape |
| Sweet Cherries | Hedelfinger | CES | 20 | Color |
| | Schmidt | HRC | 20 | Color |
| Tart Cherries | Montmorency | HRC | 20 | Color |
| Grapes | Concord | HRC | 20 | Color |
| Strawberries | All stars | Local Farm | 20 | Color/Size |
| | Earliglow | Local Farm | 20 | Color/Size |
| Sugar beets | Mono-hy-E4 | MSU Farm | 20 | Size/Shape |
| Tomatoes | Jetstar | SES | 20 | Color/Size |

TABLE 1-continued

Cultivars and general experimental conditions for all crops tested.

| Crop | Cultivar or Type | Source[z] | Storage (°C.) | Sorting Criteria |
|---|---|---|---|---|
| | Mountain Pride | SES | 20 | Color/Size |
| | Patio F | Greenhouse | 30 | Color/Size |
| | Ohio 7870 | Greenhouse | 20 & 30 | Color/Size |

[z]HRC (Horticulture Research Center,
CES (Clarksville Experimental Station),
SES (Southwestern Michigan Experimental Station)

Strawberries (*Frageria x annanassa* Duch.) were sorted into blocks with an average of 6 strawberries per sample. Sweet cherries (*Prunus avium* L.) were sorted into blocks with an average of 9 cherries per sample. 'Heidelfinger' cherries were picked one day prior to use. Tart cherries (*Prunus cerasus* L.) were sorted into blocks with an average of 9 cherries per sample. Blueberries (*Vaccinium corymbosum* L.) were sorted into blocks with an average of 20 blueberries per sample. Grapes (*Vitis lambrusca* L.) were broken into bunches, with an average of 10 grapes per bunch and 3 bunches per sample. Apples (*Malus domesticus* Borkh.) were stored at 0° C. and warmed up no more than 6 hours before use. They were sorted into blocks with an average of 3 apples per sample. Sugar beets (*Beta vulgaris* L.) were placed in 5° C. storage for 5-15 days prior to use. The beets were sorted into blocks with one beet or piece of beet per sample. Carrots (*Daucus carota* L.) were grown in 26 cm diameter by 28 cm deep clay pots and fertilized twice weekly. They were harvested on the day of the experiment. Mini-carrots had been chilled and stored prior to use. Carrots were sorted into blocks with an average of 3 carrots per sample. The field grown tomatoes (*Lycopersicon esculentum* Mill.) were picked at the MSU Southwestern Experimental Station the same day used. The greenhouse tomatoes, ('Patio F' and 'Ohio 7870'), were grown in the same size pots as the carrots and fertilized twice weekly. All tomatoes were sorted into blocks with an average of 2 tomatoes per sample.

Samples were treated either by spraying to drip with a hand sprayer or an immersion of a predetermined length. Controls were always treated with distilled water. All strawberries, sour cherries, 'Schmidt' sweet cherries, blueberries, grapes, and carrots and greenhouse grown tomatoes were picked no more than 4 hours before use.

Determination of Brix and Total Acidity

Fruit were sorted into samples according to size and stage of ripeness. The samples were treated for 1-30 minutes with either TRIA, TRIM, or 9-$\beta$-L(+) adenosine. TRIA was applied as a colloidal dispersion (Ries, S. K., CRC Crit. Rev Plant Sci. 2(3): 239-285 (1985)), in concentrations ranging from μg/liter. Crops that were subjected to desiccation after treatment were stored in plastic bags sealed with twist ties. These included strawberries, cherries, grapes, blueberries and carrots. After treatment, samples were stored at the desired temperature for 24 hours, or the duration of the time course study. They were then homogenized in a blender, (Osterizer, Sunbeam Corp, Milwaukee, Wis.) for 30 seconds and centrifuged, (IEC Centre-7R, Damon Co., Neidham Hts, Mass.) at 2800 RPM for 20-40 minutes, the time required to pellet the solids on the bottom of the tubes. The supernatant was decanted and frozen for subsequent analysis.

To determine total dissolved solids, 4-5 drops of the supernatant were placed on a zeroed digital refractometer (Atago PR-1, Tokyo, Japan) and the values recorded. To determine total acidity, 5 ml of the supernatant were added to 95 ml distilled water that had been boiled and cooled to expel dissolved gasses. It was then titrated with 0.1 N NaOH to a final pH of 8.1-8.2, and the total ml recorded.

All sugar beet, carrot, asparagus and cherry samples were ground with 1 ml/g of distilled water to facilitate homogenization. Apple samples were squeezed through a cheese cloth after homogenization to obtain clear juice. All sugar beet experiments were titrated with 0.01 N NaOH since they were low in acid content. Incubation times were between 16 and 3200 minutes in time course experiments.

Statistical Analysis

Randomized complete block designs were used for all single factor test. In experiments with two or more factors, split-plot designs were used with treatments as subplots. The number of blocks per experiment ranged from 3-6. The results of all tests were subjected to analysis of variance, including trend analysis when applicable. Mean separation was by Fisher's LSD test or by relevant F tests with single degrees of freedom.

EXAMPLE 1

Tomatoes—Seventeen experiments were conducted with 5 different cultivars of tomatoes grown in either the greenhouse or the field, and 10 of them responded to treatment with TRIA and/or 9-$\beta$-L(+) adenosine. Two experiments with 'Smallfry' tomatoes and one experiment with 'Mountain Pride' showed no response to treatment (data not shown). The 20% higher brix and 44% higher acid concentration in controls of 'Smallfry' tomatoes compared to other cultivars studied may explain why they did not respond to treatment. The most common result was a decrease in total acidity and a corresponding increase in the brix/acid ratio using either TRIA or 9-$\beta$-L(+) adenosine.

TABLE 2

Response of mature field grown 'Jetstar' tomatoes to 9-$\beta$-L(+) adenosine after a one minute immersion and storage at 20° C.

| Chemical | Concn (μg/liter) | Brix (%) | Acid (ml) | Brix/Acid ratio |
|---|---|---|---|---|
| Control | 0 | 4.67 | 3.16 | 1.66 |
| L(+) adenosine | 1 | 4.50 | 2.80 | 1.84 |
| L(+) adenosine | 10 | 4.65 | 2.73 | 2.02 |
| LSD 5% | | NS | .22 | .17 |
| LSD 1% | | NS | .32 | .25 |

TABLE 3

Response of mature 'Ohio 7870' tomatoes to high concentrations of TRIA after a one minute immersion and storage at 30° C.

| Chemical | Concn (μg/liter) | Brix (%) | Acid (ml) | Brix/Acid ratio |
|---|---|---|---|---|
| Control | 0 | 5.38 | 3.68 | 1.46[z] |
| TRIA | 1 | 5.43 | 3.40 | 1.60 |
| TRIA | 100 | 5.23 | 3.38 | 1.55 |
| TRIA | 1000 | 5.38 | 3.85 | 1.41 |

[z]F value for quadratic trend with concentration significant at the 5% level.

The change in brix varied with the application of both chemicals. Tomatoes immersed in TRIA and stored at 30° C. showed an 11.2% decrease in brix and a 16.6% decrease in acidity.

TABLE 4

Response of mature 'Ohio 7870' tomatoes to TRIA after a 30 minute immersion and storage at 30° C.

| Chemical | Concn (µg/liter) | Brix (%) | Acid (ml) | Brix/Acid ratio |
|---|---|---|---|---|
| Control | 0 | 6.45 | 4.15 | 1.56 |
| TRIA | 0.1 | 5.73 | 3.46 | 1.67 |
| TRIA | 1.0 | 6.30 | 3.85 | 1.64 |
| TRIA | 10.0 | 6.65 | 4.17 | 1.60 |
| LSD 5% | | .63 | .62 | NS |

Regardless of storage temperature of 20° C. (Table 2, as well as Table 9, hereinafter (Example 7)) or 30° C. (Tables 3, 4), the tomatoes responded to treatment with both chemicals. Seven experiments similar to the ones presented had no statistically significant differences in either the brix or total acidity (data not shown). There is no obvious explanation for this discrepancy.

EXAMPLE 2

Apples—Four experiments were conducted with 'Idared' apples, 3 of them treated for 30 minutes and one treated for one minute. In one of these tests the brix was increased by TRIA treatment an average of 6.8% (Table 5).

TABLE 5

Response of 'Idared' apples to TRIA after a 30 minute immersion and storage at 30° C.

| Chemical | Concn (µg/liter) | Brix (%) | Acid (ml) | Brix/Acid ratio |
|---|---|---|---|---|
| Control | 0 | 12.88$^z$ | 5.36 | 2.41 |
| TRIA | .01 | 13.50 | 5.58 | 2.43 |
| TRIA | 1.0 | 13.90 | 5.93 | 2.36 |
| TRIA | 100.0 | 13.88 | 5.73 | 2.43 |

$^z$F value for linear trend with concentration significant at the 5% level.

Two others showed similar increases with TRIA and 9-β-L(+) adenosine that were not statistically significant, but with an average increase in brix of 6.1% (data not shown). In the fourth experiment there was an average decrease in brix of 1.8% that was not statistically significant. Since the zero time controls were higher than either the controls or treatments, this increase in brix in three experiments can be attributed to slowing the decrease in brix normally associated with storage.

Two experiments were conducted with 'Mutsu' apples, under similar conditions. In one test, treatment of the apples with TRIA decreased the total acidity by 6.9% (Table 6), but another test showed no response to either chemical (data not shown).

TABLE 6

Response of 'Mutsu' apples to TRIA and 9-β-L(+) adenosine after a 5 minutes immersion and storage at 30° C.

| Chemical | Concn (µg/liter) | Brix (%) | Acid (ml) | Brix/Acid ratio |
|---|---|---|---|---|
| Control | 0 | 16.18 | 2.74 | 5.97 |
| TRIA | 1.0 | 16.07 | 2.55$^z$ | 6.45 |
| L(+) adenosine | 0.1 | 16.20 | 2.59 | 6.46 |
| L(+) adenosine | 10.0 | 16.30 | 2.78 | 5.93 |

$^z$F value for difference from control significant at the 5% level.

This response is very different from that of the 'Idared' apples because there was no change in brix and the total acidity decreased. The condition of the apples at treatment may have affected the response since these 2 cultivars would be expected to ripen similarly. Both cultivars had been stored before use, but the 'Idared' apples showed more storage disorders such as bruises and fungal infections than the 'Mutsu' apples.

EXAMPLE 3

Carrots—In a single test, mini-carrots showed a 7.2% decrease in brix when treated with 1 µg/liter of TRIA. The F value for the difference from control was significant at the 5% level.

Two other experiments with carrots were conducted under similar conditions. One experiment showed a significant increase in weight loss for the treatments over the controls at the 5% level, although the magnitude of the change was small, less than 1% of the total weight. In the other experiment there were no significant differences between treatments.

EXAMPLE 4

Strawberries—In an experiment conducted with 'Allstars' in 1988, there was a 7.3% decrease in brix and a 10.6% decrease in the brix/acid ratio after treatment with a high concentration (100 µg/liter) of 9-β-L(+) adenosine, and a 6.2% increase in the brix/acid ratio with TRIA (Table 7).

TABLE 7

Response of mature 'Allstars' strawberries to TRIA, TRIM and 9-β-L(+) adenosine after a one minute immersion and storage at 20° C.

| Chemical | Concn (µg/liter) | Brix (%) | Acid (ml) | Brix/Acid ratio |
|---|---|---|---|---|
| Control | 0 | 6.58 | 2.59 | 2.55 |
| TRIA | 10 | 6.70 | 2.48 | 2.71$^z$ |
| TRIM | 20,000 | 6.55 | 2.56 | 2.57 |
| L(+) adenosine | 10 | 6.52 | 2.71 | 2.42 |
| L(+) adenosine | 100 | 6.10$^z$ | 2.69 | 2.28$^z$ |
| LSD 5% | | .58 | NS | .28 |

$^z$F value for the difference from average of all treatments significant at the 5% level This is in contrast to an experiment conducted in 1989 with 'Earliglow' showing an increase in brix of 11.6% with 9-β-L(+) adenosine (Table 12). Since the fruit of both cultivars were fully ripe when tested and had approximately the same brix concentration, other factors may have influenced the response.

EXAMPLE 5

Sweet Cherries—All sweet cherry experiments were conducted with 'Schmidt' cherries except one, conducted with 'Hedelfinger', which showed no response (data not shown). In the experiment with 'Schmidt' cherries in 1988, the brix and the brix/acid ratio decreased when the samples were treated with 9-β-L(+) adenosine (Table 8).

TABLE 8

Response of 'Schmidt' sweet cherries to TRIA and 9-β-L(+) adenosine when sprayed to drip and stored at 20° C.

| Chemical | Concn (µg/liter) | Brix (%) | Acid (ml) | Brix/Acid ratio |
|---|---|---|---|---|
| Control | 0 | 7.80 | 1.02 | 7.95 |
| TRIA | 1.0 | 7.73 | 1.03 | 7.77 |
| TRIA | 10.0 | 7.68 | 1.00 | 8.03 |
| L(+) adenosine | 1.0 | 7.55$^z$ | 1.05 | 7.49$^z$ |
| L(+) adenosine | 10.0 | 7.51$^z$ | 1.05 | 7.48$^z$ |

$^z$F value for the difference from control significant at the 5% level.

Experiments show a change in acid dependent on the stage of maturity of the fruit at treatment and are presented later (Table 13).

EXAMPLE 6

Summary of non-responsive crops—There were no statistically different responses in the brix, total acidity or the brix/acid ratio in experiments with any of the following crops: asparagus, sour cherries, grapes, blueberries and sugar beets. Both TRIA and 9-$\beta$-L(+) adenosine were applied by immersion of all of these crops. Two experiments were conducted with asparagus, both with a one minute treatment of 1.0 $\mu$g/liter of TRIA. Two experiments were conducted with blueberries which were treated for one minute with 1.0 $\mu$g/liter TRIA, 1.0 mg/liter TRIM or 9-$\beta$-L(+) adenosine at 1.0 and 10.0 $\mu$g/liter. One experiment was conducted with 'Montmorency' sour cherries. They were treated with 10.0 $\mu$g/liter TRIA and 10.0 $\mu$g/liter 9-$\beta$-L(+) adenosine for 2 minutes. Two experiments with 'Concord' grapes were conducted using TRIA and 9-$\beta$-L(+) adenosine at 1.0 and 10.0 $\mu$g/liter, and TRIM at 1.0 mg/liter. Three experiments with sugar beets were performed. The beets were treated with 1.0 $\mu$g/liter TRIA and 1.0 and 100.0 $\mu$g/liter of 9-$\beta$-L(+) adenosine. The difficulty in accurate sampling of beets may have contributed to the lack of significant results.

In addition to studying the response of different fruits and vegetables to TRIA and 9-$\beta$-L(+) adenosine under similar conditions, other factors such as concentration, stage of maturity, and length of storage were considered.

EXAMPLE 7

Figure 1:
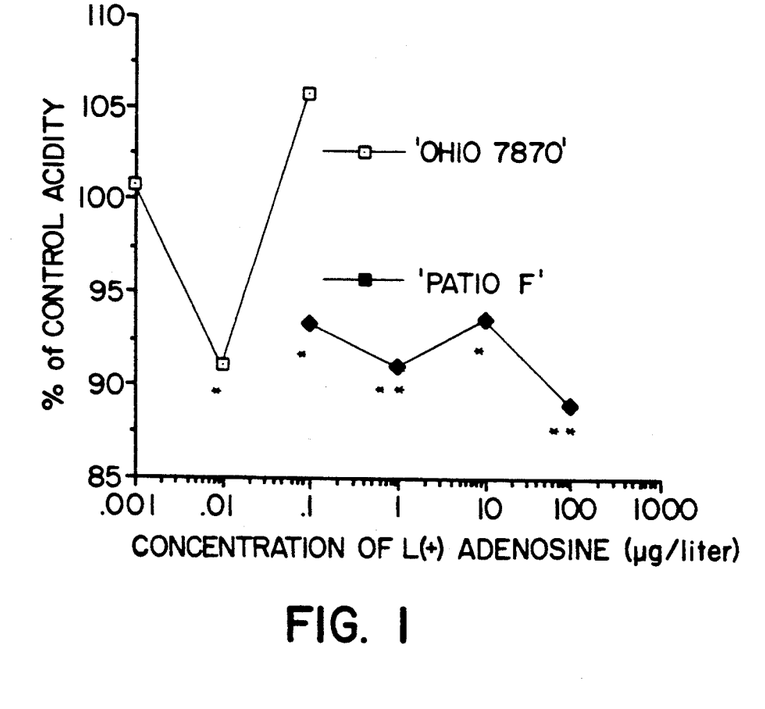
FIG. 1 shows the change in total acidity in 2 tomato cultivars treated with different concentrations of 9-β-L(+) adenosine. An *, ** indicates a difference from control significant at the 5% and 1% level respectively.

Concentration and Cultivar—The response of fruits and vegetables to different concentrations of TRIA and 9-$\beta$-L(+) adenosine was variable. In some experiments, there was no clear response to dose. In two tomato experiments using different cultivars, 9-$\beta$-L(+) adenosine applied in concentrations from 0.001–100 $\mu$g/liter decreased the total acidity, but not in a consistent pattern (FIG. 1). In other experiments there was a consistent response to concentration. In two tests with 'Ohio 7870' and 'Jetstar' tomatoes, a crude extract of the TRIA second messenger, (TRIM), at 1.0 mg/liter was more effective than other concentrations in increasing the brix (Table 9). The tests may have been complicated by other factors, such as chemicals penetrating the cuticle of the samples to a variable extent, or there may be no optimum concentration of chemical for the response, but rather a range of concentrations over which it is effective.

TABLE 9

Response of 2 tomato cultivars to different concentrations of TRIM after a one minute immersion and storage at 20° C.

| Cultivar | TRIM (mg/liter) | Brix (%) | Statistical analysis |
|---|---|---|---|
| 'Jetstar' | 0 | 4.98 | LSD 5% = .28 |
|  | 1 | 5.36 |  |
|  | 10 | 5.26 |  |
| 'Ohio 7870' | 0 | 4.92$^z$ | $^z$F value for quadratic trend with concentration significant at the 5% level |
|  | 1 | 5.15 |  |
|  | 100 | 4.92 |  |

EXAMPLE 8

Stage of Maturity—The response of all crops to both chemicals was related to the maturity of the fruit at the time it was treated. The magnitude of the response to the chemical was correlated with the stage of maturity in studies with tomatoes. The less mature fruit was not as responsive to treatment with either TRIA or 9-$\beta$-L(+) adenosine (Table 10, 11).

TABLE 10

Response of 'Patio F' tomatoes at different stages of development to TRIA and 9-$\beta$-L(+) adenosine after a 30 minute immersion and storage at 30° C.

| Chemical | Concn ($\mu$g/liter) | Acid (ml) 100% Red | Acid (ml) 40–60% Red |
|---|---|---|---|
| Control | 0 | 3.94 | 3.74 |
| TRIA | .1 | 3.64$^z$ | 3.66 |
| TRIA | 1.0 | 3.80 | 3.68 |
| L(+) Adenosine | 1.0 | 3.53$^y$ | 3.66 |
| L(+) Adenosine | 10.0 | 3.44$^y$ | 3.67 |

$^{z,y}$F value for the difference from control significant at the 5% and 1% level respectively.

TABLE 11

Response of 'Ohio 7870' tomatoes at 2 stages of development to TRIA after a one minute immersion and storage at 20° C.

| Chemical | Concn ($\mu$g/liter) | Brix/acid ratio 100% Red | Brix/acid ratio 5–25% Red |
|---|---|---|---|
| Control | 0 | 1.49 | 1.49 |
| TRIA | 1 | 1.56$^z$ | 1.53 |
| TRIA | 100 | 1.47 | 1.46 |

$^z$F value for difference from control significant at the 5% level.

In strawberries, the altered response at different stages of maturity was more dramatic. Treatment with either chemical raised the brix, but with differing magnitudes at different stages of maturity (Table 12). TRIA increased the brix in the less ripe, orange strawberries, while 9-$\beta$-L(+) adenosine increased the brix in the more mature, red ripe strawberries. TRIA increased the sugar/acid ratio only at one stage of maturity.

TABLE 12

Response of 'Earliglow' strawberries to TRIA and 9-$\beta$-L(+) adenosine when given a spray to drip treatment at different stages of development and stored at 20° C.

| | | Maturity | | | | | |
|---|---|---|---|---|---|---|---|
| Chemical | Concentration ($\mu$g/liter) | Orange Brix (%) | Red Brix (%) | Dk. Red Brix (%) | Orange Brix/acid ratio | Red Brix/acid ratio | Dk. Red Brix/acid ratio |
| Control | 0 | 7.5 | 7.4 | 7.3 | .938 | 1.08 | 1.09 |
| TRIA | 1.00 | 8.3 | 7.8 | 7.6 | 1.04 | 1.07 | 1.07 |
| L(+) adenosine | 0.01 | 7.2 | 8.0 | 7.7 | .923 | 1.13 | 1.21 |
| L(+) adenosine | 1.00 | 7.6 | 8.2 | 7.6 | .981 | 1.14 | 1.11 |
| L(+) adenosine | 100.00 | 7.6 | 7.7 | 7.5 | .958 | 1.07 | 1.19 |

Brix: LSD 5% for means within same maturity = .52
Brix/acid ratio: the interaction of TRIA X maturity is significant at the 5% level.

An experiment with 'Schmidt' sweet cherries showed a decrease in the total acidity when the cherries were treated with either TRIA or 9-$\beta$-L(+) adenosine. Both chemicals lowered the total acidity, but the magnitude of the changes was different depending on the stage of maturity of the fruit at treatment (Table 13).

TABLE 13

Response of 'Schmidt' sweet cherries at different stages of development to a spray treatment of TRIA or 9-β-L(+) adenosine and storage at 20° C.

| Chemical | Concentration (μg/liter) | Purple | Purple & Red Acid (ml) | Red |
|---|---|---|---|---|
| Control | 0 | 2.32 | 2.34 | 2.33 |
| TRIA | 1 | 2.19 | 2.25 | 2.19 |
| L(+) adenosine | 1 | 2.12 | 2.28 | 2.29 |

LSD 5% for the interaction of treatment × maturity: 0.14

Sweet cherries responded similarly to strawberries and tomatoes in that immature fruit treated with the chemicals did not show the same change in brix, total acidity, or the brix/acid ratio as mature fruit. This similar response for 3 different fruit species indicates that there is probably some basic ripening process common to most fruits affected by the chemicals. The process must change as the fruit matures, resulting in the observed differences in response at different stages of maturity.

Figure 2:
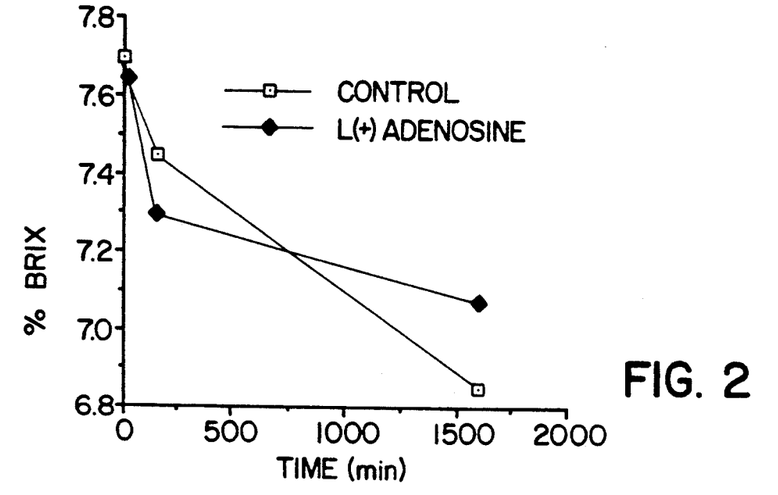
FIG. 2 shows the change in brix with time in 'Earliglow' strawberries sprayed with 1.0 μg/liter 9-β-L(+) adenosine. The F value for the interaction of time X treatment was significant at the 5% level.
Figure 3:
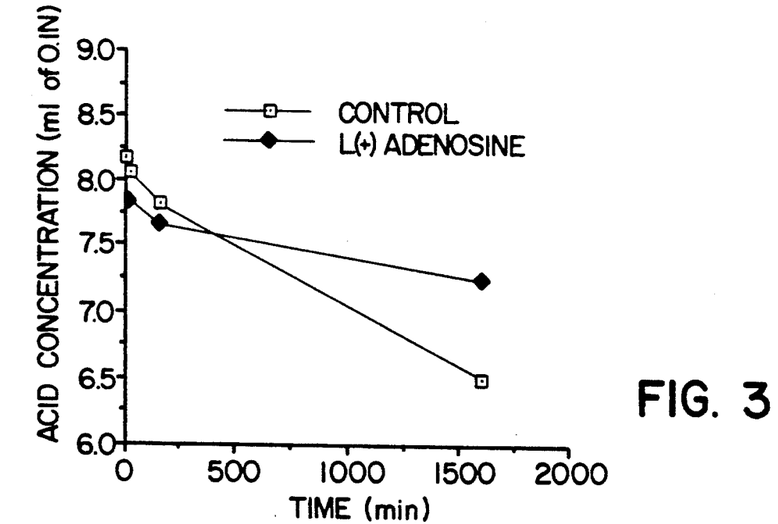
FIG. 3 shows the change in total acidity with time in 'Earliglow' strawberries sprayed with 1.0 μg/liter 9-β-L(+) adenosine. The F value for the interaction of time X treatment was significant at the 5% level.
Figure 4:
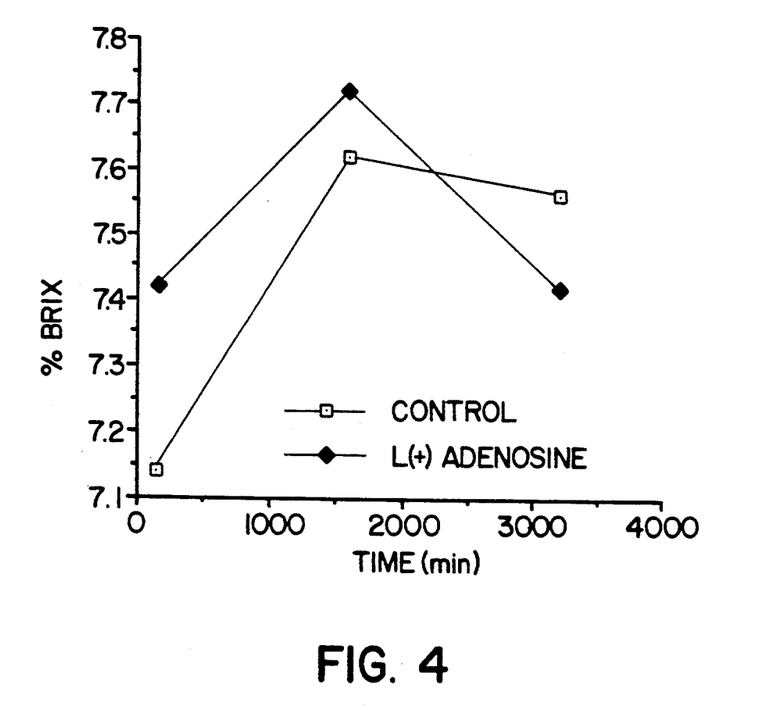
FIG. 4 shows the change with time of % brix in 'Schmidt' sweet cherries after spraying with 1.0 μg/liter of 9-β-L(+) adenosine. The F value for the interaction of time X treatment was significant at the 5% level.

Length of time in storage—In order to investigate how the response changed over time, experiments were conducted with both strawberries and sweet cherries, with the length of time in storage ranging from 16 minutes to 48 hours. The response varies over time and is not the same for all fruits. In strawberries, the brix and total acidity decreased over time in the control fruits, but treatment with 9-β-L(+) adenosine slowed the rate of loss of both parameters (FIGS. 2, 3). In 'Schmidt' cherries the brix increased more in the 9-β-L(+) adenosine treated fruit after 160 minutes, and showed no significant change thereafter (FIG. 4). In these tests, using 9-β-L(+) adenosine on strawberries resulted in long term increases in brix and total acidity over the controls, while in cherries the only significant increases in brix were over the short term.

It is intended that the foregoing description be only illustrative of the present invention and that the present invention be limited only by the hereinafter appended claims.

I claim:

1. A method for improving the quality of a part to be consumed which is removed from a plant which comprises:
    (a) applying a growth stimulant selected from the group consisting of L(+) adenosine and 1-triacontanol to the part after the part is removed in an amount sufficient to improve the quality of the part; and
    (b) holding the part until the quality of the part is improved prior to consumption of the part.

2. The method of claim 1 wherein the L(+) adenosine is in water containing between about 0.01 and 10,000 μg/liter of L(+) adenosine.

3. The method of claim 1 wherein the plant part is a fruit or vegetable.

4. The method of claim 3 wherein the plant part is a tomato as the fruit.

5. A method for changing a sugar to acid ratio in a part with such ratio which is removed from a plant to be consumed which comprises:
    (a) applying a growth stimulant selected from L(+) adenosine and triacontanol and mixtures thereof to the removed part in an amount sufficient to modify the sugar to acid ratio of the part; and
    (b) holding the part until the sugar to acid ratio is changed prior to consumption.

6. The method of claim 5 wherein the L(+) adenosine is in an aqueous solution containing between about 0.01 and 10,000 μg/liter of L(+)adenosine.

7. The method of claim 5 wherein the triacontanol is in an aqueous solution containing between about 0.01 and 100 μg/liter of triacontanol.

8. The method of claim 5 wherein the plant part is a fruit or vegetable.

9. The method of claim 8 wherein the sugar to acid ratio is increased by the growth stimulant wherein the plant part is selected from the group consisting of a tomato, strawberries and cherries as the fruit.

* * * * *

UNITED STATES PATENT AND TRADEMARK OFFICE
CERTIFICATE OF CORRECTION

PATENT NO. : 5,217,738
DATED : June 8, 1993
INVENTOR(S) : Ries

It is certified that error appears in the above-indentified patent and that said Letters Patent is hereby corrected as shown below:

Column 5, line 58, after "from", --0.1 - 1000-- should be inserted.

Signed and Sealed this

First Day of February, 1994

Attest:

BRUCE LEHMAN

Attesting Officer     Commissioner of Patents and Trademarks